(12) United States Patent
Delarcina Junior et al.

(10) Patent No.: US 9,198,848 B2
(45) Date of Patent: Dec. 1, 2015

(54) **PROCESS FOR OBTAINING EXTRACTS CONTAINING METHYLXANTHINE DERIVATIVES FROM CAKES OF PLANTS OF THE GENUS *THEOBROMA*, AS WELL AS COMPOSITION AND USE OF SAID EXTRACT**

(75) Inventors: Sergio Delarcina Junior, São Paulo-SP (BR); Cintia Rosa Ferrari, Carapicuiba SP (BR)

(73) Assignee: Natura Cosmeticos S.A., Itapecerica da Serra-SP (BR)

( * ) Notice: Subject to any disclaimer, the term of this patent is extended or adjusted under 35 U.S.C. 154(b) by 680 days.

(21) Appl. No.: 13/139,083

(22) PCT Filed: Dec. 11, 2009

(86) PCT No.: PCT/BR2009/000408
§ 371 (c)(1),
(2), (4) Date: Oct. 5, 2011

(87) PCT Pub. No.: WO2010/066015
PCT Pub. Date: Jun. 17, 2010

(65) Prior Publication Data
US 2012/0022085 A1    Jan. 26, 2012

(30) Foreign Application Priority Data
Dec. 12, 2008 (FR) .................... 08 58545

(51) Int. Cl.
| | |
|---|---|
| *C07D 473/00* | (2006.01) |
| *A61K 8/49* | (2006.01) |
| *A61K 8/97* | (2006.01) |
| *A61K 36/185* | (2006.01) |
| *A61Q 19/06* | (2006.01) |

(52) U.S. Cl.
CPC ............... *A61K 8/4953* (2013.01); *A61K 8/97* (2013.01); *A61K 36/185* (2013.01); *A61Q 19/06* (2013.01)

(58) Field of Classification Search
CPC ..... C07D 473/00; A61K 8/4953; A61K 8/97; A61K 36/185; A61Q 19/06
USPC ............................................ 544/277
See application file for complete search history.

(56) References Cited

U.S. PATENT DOCUMENTS

| | | |
|---|---|---|
| 1,073,441 A | 9/1913 | Riddle |
| 1,855,026 A | 4/1932 | Livingston et al. |
| 1,925,326 A | 9/1933 | Kellogg et al. |
| 1,947,717 A | 2/1934 | Kellogg et al. |
| 4,755,391 A | 7/1988 | Bigalli et al. |
| 6,887,501 B2 | 5/2005 | Kealey et al. |
| 2003/0170199 A1 | 9/2003 | Leciere |
| 2006/0198932 A1 | 9/2006 | Purtle et al. |
| 2007/0043109 A1 | 2/2007 | Linter et al. |
| 2007/0258920 A1 | 11/2007 | Lecoupeau et al. |

FOREIGN PATENT DOCUMENTS

WO   WO 2004/103334 A1   12/2004

OTHER PUBLICATIONS

International Search Report and Written Opinion for International Application No. PCT/BR2009/004008, mailed Jun. 30, 2010.

*Primary Examiner* — T. Victor Oh
(74) *Attorney, Agent, or Firm* — Alston & Bird LLP

(57) ABSTRACT

The present invention refers to a process for obtaining standardized extracts of methylxanthine derivatives from cakes of plants of the genus *Theobroma* such as cacoa and cupuaçu for use in a composition having potential anti-celullite lipolytic activity.

11 Claims, 2 Drawing Sheets

PROCESS FOR OBTAINING EXTRACTS CONTAINING METHYLXANTHINE DERIVATIVES FROM CAKES OF PLANTS OF THE GENUS *THEOBROMA*, AS WELL AS COMPOSITION AND USE OF SAID EXTRACT

TECHNICAL FIELD

The present invention refers to a process for obtaining standardized extracts of methylxanthine derivatives from cakes of plants of the genus *Theobroma* such as cocoa and cupuaçu for use in a composition having potential anti-cellulite lipolytic activity.

The process described in the present invention is a new way for extracting concentrates containing methylxanthines which allows reutilizing cakes of plants of the genus *Theobroma* such as cocoa and/or cupuaçu for obtaining a concentrate extract of methylxanthine and in high recovery of actives.

BACKGROUND OF THE INVENTION

Cocoa have been known for a long time for its stimulating and lipolytic characteristics due to the presence of pseudoalcaloids belonging to the methylxanthine family such as theobromine, caffeine and theophylin, having the following structural formulas:

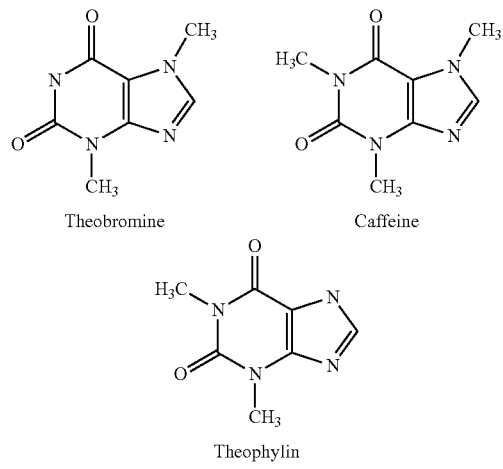

Theobromine   Caffeine

Theophylin

Pseudoalcaloids belonging to the methylxanthine family are known for their action on the inhibition of phosphodiesterase enzymes (PDE) of cyclic nucleotides, resulting in an increase in the concentration of intracellular AMPc (cyclic adesosine 3',5' phosphate) and cyclic GMP, promoting lypolisis in adipocytes. Besides that mechanism, there is also an antagonism in adenosine receptors which, when activated, promote a reduction in the accumulation of AMPc, therefore impairing lypolisis (Fredholm, B. & Lindgren E.; 1984), as well as stimulation of β-adrenergic receptors. Due to the stimulating and lypolitic characteristics of methylxantines, its use in cosmetics products for treating and preventing localized fat and celullite has been largely spread.

A number of processes for extracting methylxantines from cocoa have been described in the literature. However, the processes already disclosed in the art do not show a high yield in obtaining methylxanthines and are, in the most part, highly energy expensive and time-consuming, and besides they focus on caffeine rather than theobromine extraction, the latter usually present in concentrations smaller than caffeine in the end products obtained. This is partially due to the physical-chemical differences between caffeine and theobromine. Caffeine behaves as a weak base (pKa=14.2) and, therefore, able to solubilize in water at an acid pH and in apolar solvents at a basic pH. Theobromine, unlike caffeine, has an amphoteric behavior (pKa=10.0 and pKb=13.9) (Spiller, G. A.; 1998). Thus, theobromine is solubilized in water at extreme pHs, or too acid or too basic. Its solubilization in apolar solvents occurs in a very narrow range of pH. Thus, for concurrently extracting caffeine and theobromine in apolar solvents such as dichloromethane, a very strict control of pH in a determined range of pH is necessary.

The following documents represent the state of the art closest to the present invention. All of them relate to a process of obtaining methylxanthines from materials derived from cocoa and/or compositions containing cocoa derivatives.

U.S. Pat. No. 1,073,441: discloses a process for extracting methylxanthines by using chloroform as a solvent.

U.S. Pat. No. 1,855,026: discloses a process for extracting methylxanthines by using ethylene dichloride as a solvent.

U.S. Pat. No. 1,925,326: discloses a process for extracting methylxanthines by using tetrachloroethane as a solvent.

U.S. Pat. No. 4,755,391: this reference refers to a process for the treatment of cocoa grains and cocoa "nib" for removing methylxanthines. The process includes the aqueous extraction at between about 45° C. to about 55° C., then a series of steps of aqueous extraction at between about 90° C. to about 105° C. The use of a first aqueous extraction at low temperatures, followed by a series of steps of aqueous extraction at high temperatures, results in a greater amount of extracted theobromine.

US 2003/0170199 A1: this reference discloses a cosmetic composition containing an extract obtained from cocoa grains containing polyphenols for use for treating the skin. The extraction process used in this reference is a well-known process for grinding cocoa grains followed by hydrophylic/lypophylic separation of cocoa butter and a mixture of proteins and polyphenols.

WO 2004/103334 A1: this reference discloses a cosmetic or dermatologic composition comprising cafestol, kahweol or derivatives thereof, obtained from the extract of green coffee seeds and, optionally, a lypolithic agent as a synthetic xanthine base (caffeine or theobromine), for preventing and/or treating celullite.

Methylxanthines act as fosfodiesterase inhibitors, bringing about accumulation of intracelullar AMPc, thus establishing a signal for the increase of lypolithic activity in adipocytes. There has been shown in an ex vivo model study with adipocytes that caffeine and theobromine have equivalent power on noradrenaline-induced lypolisis. Lypolisis rate has been measured by the increase of intracelullar glycerol (Fredholm, B. & Lindgren E.; 1984). Those same researchers have demonstrated in the same work that theobromine is 50% more powerful, than caffeine in antagonizing the anti-lypolithic effects of 2-chloroadenosine, mediated by adenosine receptors. In a study of in vitro bovine fosfodiesterase inhibitors, the power of theobromine and caffeine in the ability of increasing AMPc have also be identical (Butcher, R. E & Sutherland, E. W.; 1962). Those information indicate the use of caffeine and theobromine as promising substances for the treatment of celullite in humans, at first by two distinct mechanisms, both by promoting accumulation of AMPc and inhibiting adenosine receptors.

SUMMARY OF THE INVENTION

The present invention refers to a process for obtaining an extract containing methylxanthines from cakes of plants of the genus *Theobroma* such as cocoa and/or cupuaçu, comprising the following steps:

(i) Extraction of the cake of plants of the genus *Theobroma* with an apolar solvent for removing fats;

(ii) Filtration of the product obtained in step (i) for forming a defatted cake of plants of the genus *Theobroma* and an apolar extract;

(iii) Drying the cake in vacuo, for removing traces of solvents;

(iv) Hydrolysis of the defatted and dried cake obtained in step (iii) with a strong base such as, for example, ammonium hydroxide at an optimum pH for obtaining an hydrolised extract, which increases solubility of methylxanthines, specially theobromine;

(v) Filtration;

(vi) Extraction of the aqueous phase with a solvent which can be selected from dichloromethane, ethyl acetate and chloroform, in order to obtain an apolar phase;

(vii) Drying the apolar phase with sodium sulfate, by filtration, (viii) Complete removal of the solvent contained in the apolar phase for obtaining an extract enriched with methylxanthine, specially theobromine, in a recovery of from 60 to 70% of theobromine, The process of the invention can further include the following additional steps in order to obtain crude proteins from extracts of plants of the genus *Theobroma*:

(ix) Precipitation of the crude proteins by acidification of the aqueous extract obtained in step (viii) with the addition of an acid to a pH of between 2.5 to 3.2 under constant stirring;

(x) Centrifugation of the mixture of step (ix) to collect the extract containing cocoa and/or cupuaçu crude proteins; and (xi) drying to obtain said crude proteins.

The present invention also refers to a cosmetic composition containing an extract containing methylxanthine obtained according to the above process, as well as the use of said extract for reducing celullite.

DETAILED DESCRIPTION OF THE INVENTION

Figure 1:
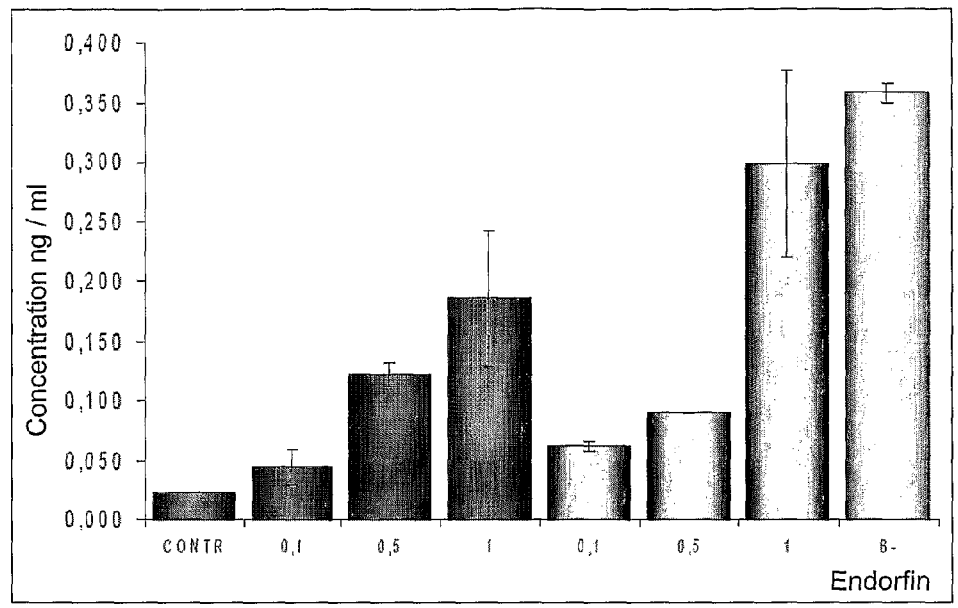
FIG. 1: Expression of β-endorphin by cultures of human keratinocytes subjected to incubation at different concentrations of extract X.

The present invention refers to a process for obtaining derivatives containing methylxanthines from cakes of plants of the genus *Theobroma* such as cocoa and/or cupuaçu. For the purposes of the present invention "cakes of plants of the genus *Theobroma*" are defined as the residues obtained upon the process for obtaining butters from the fruits of those plants, such as cocoa or cupuaçu butter, which residues are usually discarded or incinerated. The process for obtaining extracts contendo methylxanthines from cakes of plants of the genus *Theobroma* developed according to the present invention comprises the following steps:

i. Extraction of the cake of plants of the genus *Theobroma* with an apolar solvent;

ii. Filtration of the product obtained in step (i) in order to form a defatted cake and an apolar extract;

iii. Drying in vacuo;

iv. Hydrolysis of the defatted and dried cake obtained in step (iii) with a strong base for obtaining an hydrolised extract preferably having a pH from 9.5 to 10.5 since this range allows recovery of from 60 to 70% of theobromine, the molecule of which exhibits an amphoteric behavior;

v. Separation by centrifugation type decanter for 2 hours; (thus enhancing the period of time of the process, the extraction and reducing the costs)

vi. Extraction of the aqueous phase with a solvent which can be advantageously selected from dichloromethane, ethyl ether or petroleum ether, ethyl acetate and chloroform, in order to obtain an apolar phase; preferably, dichloromethane is used due to its low toxicity in humans—thus forming an emulsion;

vii. Complete removal of the solvent contained in the apolar phase, by evaporation, condensation or distillation, to obtain an extract of methylxanthines.

In another embodiment, the process of the present invention can further comprise the following steps to obtain crude protein from the fruits of plants of the genus *Theobroma*, such as cacao or cupuaçu:

i. Precipitation of the crude proteins by acidification of the aqueous extract obtained in step (vii) with the addition of an acid to a pH between 2.5 to 3.2 under constant stirring;

ii. Centrifugation of the mixture of step (viii) to collect the extract containing crude proteins; e iii. Drying in order to obtain crude proteins.

According to a preferred embodiment of the invention, the process for obtaining extracts containing methylxanthines comprises the steps of:

(a) Extraction of the cocoa cake with hexane, ethyl ether or petroleum ether, preferably hexane, and preferably at a room temperature from 25 to 30° C., for about 1 hour;

(b) Filtration of the product obtained in order to form a cake of defatted cocoa cake and the hexane or ethyl ether or petroleum ether extract, depending on the solvent used in step (a);

(c) Drying in vacuo, preferably at a temperature from 60 to 70° C., for complete removal of residual solvents;

(d) Hydrolysis of the defatted cake obtained in step (b) with a strong base such as 16% to 20% ammonium hydroxide solution for obtaining a hydrolised extract. In order to assure a better solubilization of theobromine in the aqueous phase, the hydrolisis must be carried out at a pH in the range from 9.5 to 10.5, thus assuring higher recovery of theobromine;

(e) Stirring the mixture of (d) for 1 hour at a temperature from about 25 to 30° C., more preferably at room temperature;

(f) Separation by centrifugation type decanter in order to assure a higher recovery of the aqueous extract and a shorter time of the process to take place;

(g) Extraction of the aqueous phase with dichloromethane using a liquid-liquid centrifuge at 6000 rpm in order to obtain an apolar phase. Extraction must preferably occur at a basic pH, from 9.5 to 10.5, observing the pre-fixed range of pH;

(h) Drying with anhydrous sodium sulfate, for removal of any traces of water present in the apolar phase; and (i) Complete removal of the solvent contained in the apolar phase to obtain an extract of methylxanthines. Such removal can be effected by distillation/stove drying in vacuo (pressure of 400 mmHg) at a temperature from 40 to 50° C. for 4 hours, until complete removal of dichloromethane therefrom.

As a result, an extract is obtained being at least 80% pure with 60 to 70% recovery of actives.

According to another embodiment of the present invention, the process comprises the step of centrifugating the extract obtained in step (i) with a centrifuge type decanter, preferably for increasing purification of the methylxanthine extract. Such process is simpler in comparison with other extraction processes already known, and is able to deconcentrate theobromine, to recover byproducts, to separate fats and proteins, to use known solvents and, specially, to start from residues which are usually discarded.

The process described herein, in addition to reutilize a material which would generally be discarded or incinerated, namely, cocoa and/or cupuaçu cakes, fully recovers the solvent used in the extraction step which can be reused (i) by concentrating the extract obtained upon the filtration step (ii) by distillation in vacuo (400 mmHg) of said extract containing the solvent at a temperature from 30 to 35° C. Thus, another embodiment of the present invention is the recovery of the apolar solvent used in the step of extraction of cocoa and/or cupuaçu cake.

The present invention further refers to obtaining cocoa crude proteins by the steps of acidification of the aqueous extract obtained in step (vii) with the addition of an acid to a pH between 2.5 to 3.2 under constant stirring, preferably with the addition of sulphuric acid; centrifugation of the mixture obtained using a 5-3 μm bag to collect the extract containing crude proteins from coca; and spray dryer drying in order to obtain cocoa crude proteins.

The present invention further refers to a cosmetic composition containing the extract of methylxanthines obtained by the above-described process for use as a lypolithic agent in the treatment and/or prevention of localized fats and celullite.

Moreover, in animal tests, topical administration of cocoa seed extract containing 0.017% e 0.208% caffeine and theobromine, respectively, and caffeine and theobromine, at concentration of 10 mM, were effective in preventing "deformation of UVA light-induced wrinkles at the dose of 13.0 J/cm$^2$ in a 15-week study (Mitani et al, 2007)".

EXAMPLES OF THE INVENTION

The extract of plants of the genus *Theobroma* such as cocoa and/or cupuaçu fruit obtained by the process of the present invention can be used in a number of cosmetic products. The main examples of products which can be prepared from the extract of cocoa fruit obtained according to the present invention, or from cosmetic and pharmaceutical compositions comprising said extract, are:

Face and body balsam;
After-shaving balsam;
After-depilation balsam;
Lipstick or lip gloss;
Face and body gel;
Moisturizing body milk;
Moisturizing face milk;
Moisturizing body lotion;
Moisturizing face lotion;
Products for the scalp;
Sun protectors or blockers for adult and children use, whether or not directed to use concurrently to sports practicing;
Moisturizing face and body products;
Face and body anti-age products;
Face and body firming products;
Self-tanning products;
Insect-repellant products;
Moisturizing face and body products for illuminating the skin;
Pharmaceutical preparations for topical administration;
Face and body cosmetic preparations for children use;
Cosmetic preparations of localized action, specific for the peri-ocular area, lip contour, lips, anti-spots, anti-shadows eye creams, and the like;
Anti-acne products;
Skin lighting products;
Pharmaceutical compositions for the treatment of specific dermatoses;
Lipsticks and waxy bases;
Pigmented blushes and bases;
Face powders; and
Any products for making-up the eye area.

Cosmetic and Pharmaceutical Compositions

Cosmetic and pharmaceutical compositions comprising the extract of plants of the genus *Theobroma* of the present invention can also comprise some ingredients already known from the prior art, such as emollients, sun filters, and vehicles.

The cosmetic and pharmaceutical compositions comprise a cocoa or cupuaçu extract and a suitable carrier (vehicle). Preferably the compositions of the present invention also comprise a polyphenol.

Emollients

Emollients play several roles in cosmetic compositions, inter alia: to add or replace lipids and oils naturally occurring in the skin, to solubilize sun filters, to impart a better spreadability upon administration of the product, to modify the touch, etc.

As emollients to be added to the composition of the present invention, there can be used conventional lipids such as, for example, oils, waxes, lipids and other water-insoluble ingredients and polar lipids which are lipids modified so as to increase their solubility in water by esterification of a lipid to a hydrophylic moiety such as, for example, hydroxy groups, carbonyl group inter alia. Some compounds that can be used as emollients are naturally occurring oils and those derived from plants, esters, silicone oils, polyunsaturated fatty acids, lanoline and derivatives thereof. Some naturally occurring oils that can be used are derived from apricot seed, sesame seeds, soybeans, peanuts, coconut, olive, cocoa butter, almonds, avocado, carnauba, cottonseed, rice bran, peach kernel, mango kernel, jojoba, macadamia nuts, coffee, grapeseed, pumpkin seeds, among others, and mixtures thereof.

Some ethers and esters can also serve as emollients such as, for example, $C_8$-$C_{30}$ alkyl esters of $C_8$-$C_{30}$ carboxylic acids, $C_1$-$C_6$ diol monoesteres and diesters of $C_3$-$C_{30}$ carboxylic acids, saccarose monoesters of $C_{10}$-$C_{20}$ alcohols and combinations thereof. Examples of those compounds are dicaprylic ether, cetyl lactate, isopropyl palmitate, dicaprylyl carbonate, $C_{12-15}$ alkyl benzoate, isopropyl myristate, isopropyl isononate, saccarose palmitoate, saccarose oleate, isostearyl lactate, glyceryl behenate, triglycerol-4 isostearate, carboxylic acid of lauryl pyrrolydone, pantenyl triacetate, and combinations thereof.

Silicones also act as emollients in the cosmetic and pharmaceutical compositions of the present invention. Some examples of silicone that can added to said compositions are: volatile and non-volatile silicone oils such as, for example, cyclomethicone, alkyldimethicones, dimethicone-copolyols, dimethiconols, phenyl trimethicones, caprylyl trimethicones, amino-functional silicones, phenyl-modified silicones, phenyl trimethicones, alkyl-modified silicones, dimethyl and diethyl polysiloxane, mixed $C_1$-$C_{30}$ alkyl polysiloxane, dimethyl siloxanes, polydimethylsiloxane, methyl-ω-methoxypolymethylsiloxane, polyoxydimethylsilylene, silicone polydimethyl oil and combinations thereof or silicone elastomers like cross-polymer of cyclomethicone and dimethicone, cross-polymer of vinyl dimethicone and dimethicone, cross-polymer of dimethicone and dimethicone and cross-polymer of cyclopentasiloxane and dimethicone.

Other fatty alcohols, mono-, di-ou triglycerides etheres having a lypophylic nature such as dicaprilyl ether, in addition to synthetic and naturally occurring hydrocarbons, organic carbonates such as dicaprilyl carbonate, some types of silicones such as cyclomethicone e mixtures thereof can also be used.

Moreover, several naturally occurring compounds can also be used as emollients such as, for example, microcrystalline wax, carnauba wax, karyte butter, beeswax, ozokeryte wax among others.

Sun Filters

In order to filtrate the ultraviolet radiation, sun protection agents which can be water-soluble or liposoluble can be added.

Some examples of filters absorbing ultraviolet rays that are useful to be added to the cosmetic composition of the present invention are: camphorbenzylidene and derivatives thereof, camphorisophthalylidene and camphorterephthalylidene, and derivatives thereof, cynamic acid and esters thereof, salicylic acid and esters thereof, benzoic acid and esters thereof, p-aminobenzoic acid and derivatives thereof such as its esters, substituted hydroxybenzophenones, substituted dibenzoylmethane, benzotriazole and some derivatives such as 2-arylbenzotriazole, 2-arylbenzimidazole, 2-arylbenzofurans, 2-arylbenzoxazole, 2-arylindole, mono-phenylcyanoacrylates, diphenylcyanoacrylates, among other ultraviolet filters known in the state of the art.

Some sun filters useful in the present invention are organic compounds, usually low water-soluble such as triazine derivatives (for example, hydroxyphenyltriazine compounds or benzotriazole derivatives), some amides such as those containing a vinyl group, cynamic acid derivatives, sulphonated benzimidazoles, diphenylmalonitriles, oxalilamides, camphor derivatives, salicylic acid derivatives such as 2-ethylhexyl salicylates, isopropyl homosalates and salicylates, diphenylacrylates, benzophenone derivatives such as benzophenone-2, benzophenone-3, and benzophenone-4, PABA such as 2-ethylhexyl 4-dimethylamino-benzoate, and other sun filters commonly added to compositions of products for sun protection.

In addition to the example cited hereinabove, there are other preferred ingredients to serve that purpose such as: methyl sulfate of N,N,N-trimethyl-4-(2-oxoborn-3-ylidenemethyl)anilinium; 3,3'-(1,4-phenylenedimethylene)bis(7,7-dimethyl-2-oxo-bicyclo-(2.2.1)1-heptylmethanesulfonic acid and derivatives thereof; 1-(4 tert-butylphenyl)-3-(4-methoxyphenyl)propane-1,3-dione; α-(2-oxoborn-3-ylidene)toluene-4-sulfonic acid and its potassium, sodium and triethanolamine salts; 2-ethylhexyl 2-cyano-3,3'-diphenylacrylate; 2-ethoxyethyl 4-methoxycinnamate; 2,2'-dihydroxy-4-methoxybenzophenone; methyl anthranilate; triethanolamine salicylate; 2,2',4,4' tetrahydroxybenzophenone; 2-phenylbenzimidazol-5-sulfonic acid and its potassium, sodium and triethanolamine salts; 2-ethylhexyl 4-methoxycinnamate; 2-hydroxy-4-methoxybenzophenone (oxybenzone); 2-hydroxy-4-methoxybenzophenone 5-sulfonic acid and its sodium salt (sulisobenzone e sodium sulisobenzone); 4 aminobenzoic acid PABA; homomethyl salicylate; N-{(2 e 4) [(2 oxoborn-3-ylideno) methyl]benzyl}acrylamide polymer; titanium dioxide (with or without a lipophylic coating); ethyl N-ethoxy-4-aminobenzoate; 2-ethylhexyl 4-dimethylaminobenzoate; 2-ethylhexyl salicylate; isopentyl 4-methoxycinnamate; 3-(4'-methylbenzilide-no)-d-1-camphor; 3-benzylidene camphor; 2,4,6-trianilin-(p-carbo-2'-ethyl-hexyl-l'-oxy)-1,3,5-triazine octyl, zinc oxide (with or without a lipophylic coating); 2-(2H-benzotriazole-2-yl)-4-methyl-6-{2-methyl-3-(1,3,3, 3-tetramethyl-1-((trimethylsylyl)oxy)disiloxanyl) propyl}phenol; benzoic acid; 4,4'-[[6-[[4-[[(1,1-dimethyl-ethyl)amino]carbonyl]phenyl]amino]-1,3,5-trazine-2,4-diyl]diimino]bis, bis(2 ethylhexyl); 2,2'-methylene-bis-6-(2H-benzotriazole-2-il)-4-(tetramethyl butyl)-1,1,3,3-phenol; methyleno bis-benzotriazolyl tetraethyl butyl phenol; monosodium salt of 2,2'-bis-(1,4-phenylene)-1H-benzimidazole-4,6 dissulfonic acid; (1,3,5)-triazine-2,4-bis{[4-(2-ethyl-hexyloxy)-2-hydroxyl]-phenyl]-6-(4-methoxyphenyl); bis-ethylhexyloxyphenol methoxyphenyl triazine; methylene bis-benzotriazolyl tetramethylbutylphenol; butyl methoxydibenzoylmethane, 2-ethylhexyl p-methoxycinnamate, methylene bis-benzotriazolyl tetramethylbutylphenol, 4-butyl-4-methoxydibenzoylmethane, benzophenone 3, bis-ethylhexyloxyphenol methoxyphenyl triazine, octyl triazone, titanium dioxide, cinnamidopropyltrimonium chloride, dimethylpabamidopropyl laurdimonium tosylate.

Yet, there are other sun filters that can also act by protecting the skin such as iron oxide, titanium dioxide, titanium dioxide in combination with simethicone, zinc oxide, mono- or polycarbonyl compounds such as isathine, aloxane, ninhydrine, glyceraldehyde, mesotartaric aldehyde, glutaraldehyde, pyrazolin-4,5-dione or 4,4-dihydroxypyrazolin-5-one derivatives, methylglyoxal, 2,3-dihydroxysuccinic dialdehyde, 2-amino-3-hydroxysuccinic dialdehyde and 2-benzylamino-3-hydroxysuccinic dialdehyde.

Vehicles, Diluents or Carriers

Water is the basis for a number of possibilities of cosmetic compositions prepared from antioxidative complex already described, acting as a vehicle for the further ingredients. The compositions of the present invention comprise preferably demineralized or distilled water in an adequate percentage (q.s.) for reaching 100% of the formula based on the total weight of the present composition. Obviously, other cosmetically acceptable vehicles can be used in the present invention. In the examples of composition that will be describe hereinafter, 96° GL ethyl alcohol, oily vehicles (oils in general, waxes and butters), siliconated vehicles, and the like, can also be used as a vehicle.

Other Additional Ingredients

In order to provide the cosmetic and pharmaceutical compositions of the present invention with some desirable characteristics not conferred by the ingredients already mentioned, some optional ingredients which are compatible with the properties thereof can be added. Some of those compounds that can be added to said compositions are as follows:

Active principles (encapsulated or not): they can be lipophylic or hydrophylic, such as algae extracts, plant extracts, a combination of palmitoyl hydroxypropyl trimonium aminopectine, glycerine cross-polymer, lecithin and grapeseed extract, alpha-bisabolole (antiinflammatory active), D-panthenol (conditioning active), disaccharide gum 2 and disaccharide gum 3 and other actives commonly added to compositions of products for topical use;

Bacteriostates, bactericides or antimicrobes;

Emulsifying agents such as potassium cetylphosphate, and the like;

Stabilizing agents such as sodium chloride, and the like;

Sequestring agents such as ethylenediaminotetracetic acid (EDTA) and the salts thereof, and the like;

pH adjusting agents such as triethanolamine, sodium hydroxide, and the like;

Preservative agents such as fenoxyethanol, PEG-5 cocoate and PEG-8 dicocoate and iodopropinyl butylcarbamate e PEG-4, and the like;

Naturally or synthetically occurring colorants;

Thickening agents such as xanthan gum and carbomer, and the like;

Plant extracts: camomile, rosemary, thyme, calendula, extract of carrot, extract of juniper, extract of gentian, extract of cucumber, and the like;

Skin conditioning agents; and

Further cosmetically acceptable ingredients, which are compatible with the antioxidative complex of the present invention.

Examples of Composition

The following examples are preferable variations of compositions comprising the antioxidative complex of the present invention and shall not be construed as limitations thereof. In this regard, it is to be understood that the scope of the present invention encompasses other possible modifications, only limited by the appended claims, including all possible equivalents therein, Examples of Cosmetic Composition Gel:

| Xanthan gum | 1.0% |
|---|---|
| EDTA | 0.1% |
| Extract of enriched cocoa | 0.3% |
| Ethyl alcohol | 3.0% |
| BHT | 0.05% |
| Fenoxyethanol | 0.7% |
| Demineralized water qsp | 100% |

Emulsão:

| Xanthan gum | 0.2% |
|---|---|
| EDTA | 0.1% |
| Glycerine | 3.0% |
| Caprilic/capric triglyceride | 4.0% |
| Potassium cethyl phosphate | 2.5% |
| Extract of enriched cocoa | 0.3% |
| BHT | 0.05% |
| Fenoxyethanol | 0.7% |
| Demineralized water qsp | 100% |

In order to illustrate the effectiveness of the extracts obtained by the process described in the present application, a number of dosage of β-endorphin tests have been carried out (tests 1 to 3).

Test 1: Dosage of β-Endorphin, by the Enzymatic Method on Samples of Supernatant of Human Keratinocyte Culture.

In order to measure the concentration of human β-endorphin on samples of supernatant of human keratinocyte culture, keratinocyte cultures were incubated at different concentrations of the extract obtained according to the present invention.

Object: to measure the concentration of human β-endorphin on samples of supernatant of human keratinocyte culture.

Materials Used:

Kit "β-Endorphin ELISA" manufactured by "MD Biosciences, Inc.", catalog no. EDRF-96, lot 424706-EX, expiration date February 2007, for quantifying β-endorphin-specific peptides and those related thereto, containing:

Ready-to-use secondary antibody-sensibilized microplate

Template of lyophilized β-endorphin, rehydrated with 1 ml of assay buffer, concentration 1000 ng/mL.

Lyophilized positive control, reconstituted with 200 μL of assay buffer

Lyophilized biotinilated β-endorphin, reconstituted with 5 mL of assay buffer

Lyophilized anti-β-endorphin rabbit serum, reconstituted with 5 mL of assay buffer.

Concentrate streptavidine-peroxydase, for use diluted 1/1000 in assay buffer.

Substract—TMB solution

20-Fold concentrate assay buffer, for use diluted in distilled water 2N hydrochloric acid Peptides used in the kit: Tyr-Gly-Gly-Phe-Met-Thr-Ser-Glu-Lys-Ser-Gln-Thr-Pro-Leu-Val-Thr-Leu-Phe-Lys-Asn-Ala-Ile-Lys-Asn-Ala-Tyr-Lys-Lys-Gly-Glu Characteristics of the Assay:

1. Range: 0 to 100 ng/mL
2. Region of linearity: 0.14 to 2.51 ng/mL
3. Accuracy: intra-assay variation: <5%; inter-assay variation: <14%
4. Specificity: it shows the following degrees of cross-reactivity:
   i. human β-endorphin 100%
   ii. rat β-endorphin 100%
   iii. human Ac-β-endorphin 100%
   iv. human Met-Encefalina 0%
   v. human Leu-Encefalina 0%

"phenomenex" extraction kit lot S201-35 containing:

"STRATA C-18-E" (extraction column)

Buffer A: trichloroacetic acid (ATF) in water.

Buffer B: 60% acetonitrile in 1% trichloroacetic acid.

Test Procedure

A) Extraction of β-endorphin from the supernatant of cell culture, according to manufacturer's instructions.

1. Supernatant of human keratinocytes culture was aliquoted and stored at −70° C., until use.

2. An aliquot of each sample was thawed, homogenized, and 400 μL were acidified with the same volume of buffer A, homogenized and centrifugated 10,000 g for 20 minutes at 4° C.

3. C-18 column was equilibrated once with buffer B and three times with buffer A.

4. The sample was loaded into the column, then the column was washed twice with buffer A and eluted with buffer B.

5. The eluate was evaporated in a concentrator "speedvac", and the test tubes were stored at −20° C. until use.

B) Dosage of β-endorphin, carried out according to the manufacturer's instructions 1. Resuspension of the dehydrated sample at the initial volume with assay buffer was carried out.

2. Template was diluted in order to obtain concentrations of 100, 10, 10.1 e 0.01 ng/mL of β-endorphin.

3. 50 μL of each dilution of the template, control and samples were pippeted onto the microplate. One well was left empty for the blank of the reaction and one filled with dilution buffer for the zero point of the curve.

4. 25 μL of rabbit anti-β-endorphin were pippeted into the wells except the blank of the reaction well.

5. 25 μL of biotinilated β-endorphin were pippeted into every well except the blank of the reaction well.

6. The plate was covered and incubated for 2 hours at room temperature.

7. The plate was bubbled six times with assay buffer, except the blank well.

8. The plate was turned upside down on absorbing paper for removing any liquid.

9. 100 μL of streptavidine-peroxydase was pippeted into all wells except the blank well.

10. Procedure of item 7 was repeated.

11. 100 μL of TMS was pippeted into all wells, the blank well included.

12. This was covered and incubated for one hour at room temperature.

13. 100 μL of 2 N HCl was pippeted into all wells, the blank well included.

14. Read at 450 nm.

Results

Some aliquots were used to check variation intra- and inter-assay of the method. The variation coefficient intra-assay was 8.3% and inter-assay 19.6%.

According to the pre-determined treatment of keratinocyte cultures, the data obtained allow to define the behavior thereof relative to the expression of Bendorphin, as depicted in FIG. 1.

Test 2: Assessment of the Production of β-Endorphin in a Culture of Human Fibroblasts.

In this test samples of caffeine and TC150905MX at different concentrations (0.038 μg/mL, 0.075 μg/mL, 0.150 μg/mL, 0.300 μg/mL and 0.600 μg/mL) and control samples were compared as shown in Table 1 below:

TABLE 1

| stras Concentrations used (time of incubation) | | |
|---|---|---|
| Samples | Concentrations used (mcg/mL) | Time of incubation |
| Caffeine | 0.038 | 48 hr |
|  | 0.075 |  |
|  | 0.150 |  |
|  | 0.300 |  |
|  | 0.600 |  |
| TC150905MX | 0.038 | 48 hr |
|  | 0.075 |  |
|  | 0.150 |  |
|  | 0.300 |  |
|  | 0.600 |  |

Cell Cultures

To carry out the experiments a cell line (pure/isolated culture) of human fibroblasts, adult age (mature), 6a passage was used.

The cells were cultured on appropriate culture plates (24 well) in specific medium culture, containing supplements required for cell maintenance and proliferation. For that purpose, $1\times10^5$ cells/well were seeded, confluence being reached after a 48 hour incubation, in a wet stove, 5% $CO_2$, 37° C.

Subsequent to confluence (approximately 80% of the total area), the samples to be assessed were added, at the appropriate concentrations and previously established, according to table 1, always keeping a group as CONTROL (with no treatment), for comparative purposes in assessing effectiveness. The samples were previously diluted in proper culture medium.

After 48 hour incubation (wet stove, 5% CO2, 37° C.) with the samples, the supernatant of cell cultures were collected for assessing the beta-endorphin release. The possible citotoxicity of the compound was also assessed and taken into account. Assessment was qualitative only, by analysis of morphology and cell characteristics.

Quantification of Beta-Endorphin

Quantification of the production of beta-endorphin by the cells in culture was carried out by the immunoenzymatic method ELISA (Enzyme-Linked Immunosorbent Assay), using a kit appropriate for determining beta-endorphin in biological samples. The samples were assessed in quadruplicate.

Figure 2:
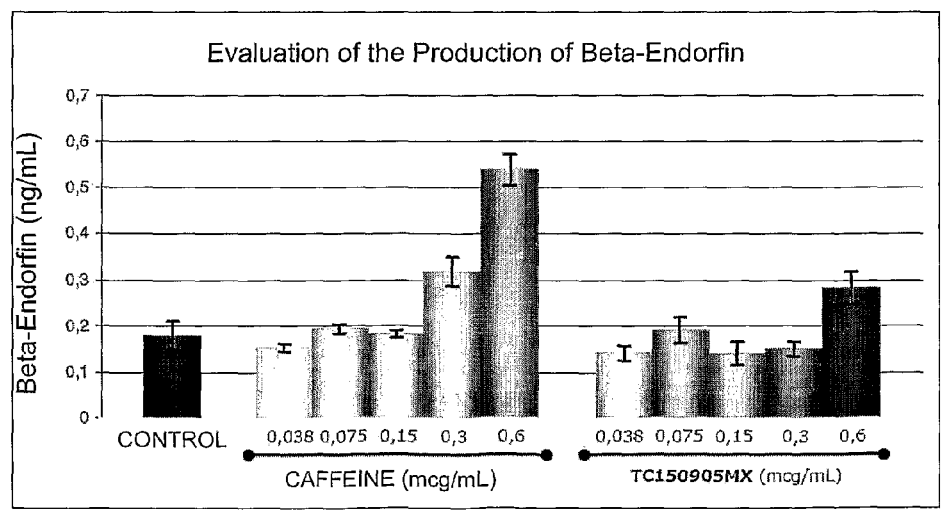
FIG. 2: Production of β-endorphin in human fibroblasts culture after incubation with samples containing different concentrations of caffeine or TC150905MX.

By analyzing FIG. 2 it is seen that the human fibroblast cultures that were incubated with samples of caffeine showed a higher production of β-endorphin if compared with the samples at the same concentration of TC150905MX.

Test 3: Assessment of the Production of β-Endorphin in a Culture of Human Keratinocytes.

In this test samples of caffeine and TC150905MX at different concentrations (0.038 μg/mL, 0.075 μg/mL, 0.150 μg/mL, 0.300 μg/mL and 0.600 μg/mL) and control samples were compared as shown in Table 2 below:

TABLE 2

| stras Concentrations used (time of incubation) | | |
|---|---|---|
| Samples | Concentrations used (mcg/mL) | Time of incubation |
| Caffeine | 0.038 | 48 hr |
|  | 0.075 |  |
|  | 0.150 |  |
|  | 0.300 |  |
|  | 0.600 |  |
| TC150905MX | 0.038 | 48 hr |
|  | 0.075 |  |
|  | 0.150 |  |
|  | 0.300 |  |
|  | 0.600 |  |

Cell Cultures

To carry out the experiments a cell line (pure/isolated culture) of human keranoticytes, adult age (mature), 7th passage was used.

The cells were cultured on appropriate culture plates (24 well) in specific medium culture, containing supplements required for cell maintenance and proliferation. For that purpose, $1\times10^5$ cells/well were seeded, confluence being reached after 72 hour incubation, in a wet stove, 5% $CO_2$, 37° C.

Subsequent to confluence (approximately 80% of the total area), the samples to be assessed were added, at the appropriate concentrations and previously established, according to table 2, always keeping a group as CONTROL (with no treatment), for comparative purposes in assessing effectiveness. The samples were previously diluted in proper culture medium.

After 48 hour incubation (wet stove, 5% $CO_2$, 37° C.) with the samples, the supernatant of cell cultures were collected for assessing the beta-endorphin release. The possible citotoxicity of the compound was also assessed and taken into account. Assessment was qualitative only, by analysis of morphology and cell characteristics.

Quantification of Beta-Endorphin

Quantification of the production of beta-endorphin by the cells in culture was carried out by the immunoenzymatic method ELISA (Enzyme-Linked immunosorbent Assay), using a kit appropriate for determining de beta-endorphin in biological samples. The samples were assessed in quadruplicate.

Figure 3:
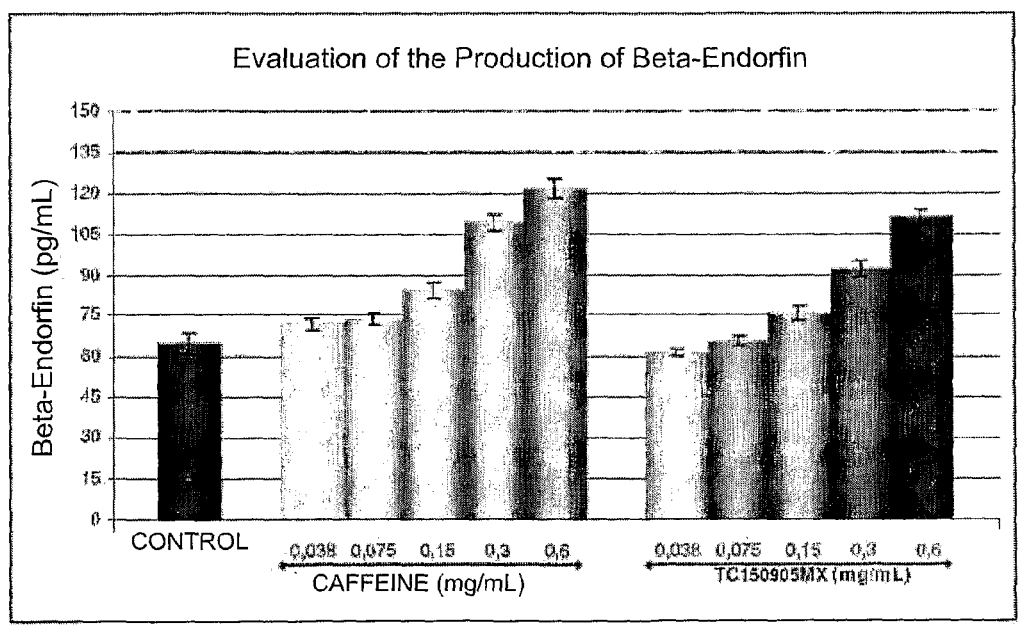
FIG. 3: Production of β-endorphin in human keratinocytes culture after incubation with samples containing different concentrations of caffeine or TC150905MX.

By analyzing FIG. 3 it is seen that the human keratinocyte cultures that were incubated with samples of caffeine showed a higher production of β-endorphin if compared with the samples at the same concentration of TC150905MX.

The invention claimed is:

1. Process for obtaining extracts containing methylxanthine derivatives from cakes of plants of the genus *Theobroma*, wherein the process comprises the following steps:

i. extracting cake of plants of the genus *Theobroma* with an apolar solvent;
ii. filtering a product obtained in step (i) for forming a defatted cake of plants of the genus *Theobroma* and an apolar extract;
iii. drying in vacuo the defatted cake obtained in (ii);
iv. hydrolyzing of the defatted and dried cake obtained in step (iii) with a strong base for obtaining a hydrolyzed extract at a pH of 9.5 to 10.5;
v. separating the resulting product from step (iv) by centrifugation;
vi. extracting of an aqueous phase to obtain an apolar phase; and
vii. removing solvent contained in the apolar phase obtained in step (vi), to obtain an extract of methylxanthines.

2. Process as claimed in claim 1, wherein said process comprises the steps of:
i. extracting cake of plants of the genus *Theobroma* with hexane, ethyl ether or petroleum ether;
ii. filtering a product obtained for forming a defatted cake of plants of the genus *Theobroma* and the hexane or ethyl ether or petroleum ether extract;
iii. drying in vacuo, at a temperature from 60 to 70° C.;
iv. hydrolyzing of the defatted cake obtained in step (ii) with 16% a 20% ammonium hydroxide solution for obtaining a hydrolyzed extract;
v. separating by decanter type centrifugation;
vi. extracting of the aqueous phase with dichloromethane using a liquid-liquid centrifuge at 6000 rpm in order to obtain an apolar phase, and
vii. removing solvent contained in the apolar phase to obtain an extract of methylxanthines.

3. Process as claimed in claim 2, wherein the step of removing of solvent is carried out by distillation and drying at a temperature from 40 to 50° C. for 4 hours.

4. Process for obtaining crude proteins from cakes of plants of the genus *Theobroma*, wherein said process comprises the following steps:
i. extracting of the cake of plants of the genus *Theobroma* with an apolar solvent;
ii. filtering a product obtained in step (i) for forming a defatted cake of plants of the genus *Theobroma* and an apolar extract;
iii. drying in vacuo the defatted cake obtained in (ii);
iv. hydrolyzing of the defatted and dried cake obtained in step (iii) with a strong base for obtaining a hydrolyzed extract at a pH of 9.5 to 10.5;
v. separating of the resulting product from step (iv) by centrifugation;
vi. extracting an aqueous phase;
vii. removing solvent contained in the apolar phase obtained in step (vi), to obtain an extract of methylxanthines;
viii. acidifying of the aqueous extract obtained in step (vii) with the addition of an acid to a pH between 2.5 to 3.2 under constant stirring;
ix. centrifuging of the mixture of step (viii) to collect the extract containing said crude proteins; and
x. drying the product obtained in (ix) in order to obtain crude proteins.

5. Process as claimed in claim 4, wherein said process comprises the steps of:
i. Extraction of the cake of plants of the genus *Theobroma* with hexane, ethyl ether or petroleum ether;
ii. Filtration of the product obtained for forming a defatted cake of plants of the genus *Theobroma* and the hexane or ethyl ether or petroleum ether extract;
iii. Drying in vacuo the defatted cake obtained in (ii), at a temperature from 60 to 70° C.;
iv. Hydrolysis of the defatted cake obtained in step (iii) with 16% to 20% ammonium hydroxide solution for obtaining a hydrolyzed extract;
v. Separation by decanter type centrifugation;
vi. Extraction of the aqueous phase with dichloromethane using a liquid-liquid centrifuge at 6000 rpm in order to obtain an apolar phase,
vii. Complete removal of the solvent contained in the apolar phase to obtain an extract of methylxanthines,
viii. Acidification of the aqueous extract obtained in step (vii) by the addition of sulphuric acid to a pH between 2.5 to 3.2 under constant stirring;
ix. Centrifugation of the mixture of step (viii) using a 5-3 μm bag to collect the extract containing said crude proteins; and
x. Spray drier drying in order to obtain crude proteins.

6. Process as claimed in claim 5, wherein the step of removal of solvent is carried out by distillation and drying at a temperature from 40 to 50° C. for 4 hours.

7. Process as claimed in claim 1, wherein said process further comprises the step of stirring the mixture from step (iv) for 1 hour at a temperature from about 25 to 30° C.

8. Process as claimed in claim 7, wherein said process further comprises, after step (vi), the step of drying with anhydrous sodium sulfate, for removal of any traces of water present in the apolar phase.

9. Process as claimed in claim 1, wherein the plants of the genus *Theobroma* are cocoa and cupuaçu.

10. A process for preparing a cosmetic composition which comprises preparing an extract containing methylxanthines derivatives from cakes of plants of the genus *Theobroma*, wherein the process comprises the following steps:
i. Extraction of the cake of plants of the genus *Theobroma* with an apolar solvent;
ii. Filtration of the product obtained in step (i) for forming a defatted cake of plants of the genus *Theobroma* and an apolar extract;
iii. Drying in vacuo the defatted cake obtained in (ii);
iv. Hydrolysis of the defatted and dried cake obtained in step (iii) with a strong base for obtaining a hydrolyzed extract at a pH of 9.5 to 10.5;
v. Separation of the resulting product from step (iv) by centrifugation;
vi. Extraction of the aqueous phase;
vii. Complete removal of the solvent contained in the apolar phase obtained in step (vi), to obtain an extract of methylxanthines; and
viii. Adding cosmetically acceptable excipients, vehicles, diluents and carriers.

11. Process as claimed in claim 10, wherein the plants of the genus *Theobroma* are cocoa and cupuaçu.

* * * * *